United States Patent [19]
Tillman et al.

[11] Patent Number: 6,090,602
[45] Date of Patent: Jul. 18, 2000

[54] LEVO-MONOSACCHARIDE IN A NUCLEOSIDE ANALOG FOR USE AS AN ANTI-RETROVIRAL AGENT

[75] Inventors: Timothy N. Tillman; Daryl L. Thompson; Gordon J. Rafool, all of Winter Haven, Fla.

[73] Assignee: Promelas Research Corporation, Winter Haven, Fla.

[21] Appl. No.: 09/025,530

[22] Filed: Feb. 18, 1998

[51] Int. Cl.$^7$ ............................. C12N 9/00; C12N 15/63; C07H 21/04
[52] U.S. Cl. ................... 435/183; 435/320.1; 435/372.3; 536/24.5
[58] Field of Search ................................ 435/6, 69.2, 88, 435/183, 320.1, 372.3; 536/23.1, 24.33, 24.5; 514/44

[56] References Cited

U.S. PATENT DOCUMENTS

| | | | |
|---|---|---|---|
| 4,970,199 | 11/1990 | Durette et al. | 514/26 |
| 5,559,101 | 9/1996 | Weis et al. | 514/45 |
| 5,561,120 | 10/1996 | Lin et al. | 514/49 |
| 5,565,438 | 10/1996 | Chu et al. | 514/50 |
| 5,567,688 | 10/1996 | Chu et al. | 514/46 |
| 5,567,689 | 10/1996 | Sommadossi et al. | 514/50 |
| 5,587,362 | 12/1996 | Chu et al. | 514/46 |
| 5,627,160 | 5/1997 | Lin et al. | 514/49 |
| 5,631,239 | 5/1997 | Lin et al. | 514/49 |
| 5,658,880 | 8/1997 | Dasgupta et al. | 514/8 |
| 5,672,594 | 9/1997 | Weis et al. | 514/45 |

OTHER PUBLICATIONS

Wilson et al. Antimcrobial Agents and Chemotherapy 37(8), 1720–1722 (Aug. 1993).

Davis et al. Antiviral Res. 30, 133–145 (1996).

B. Sheid, L. M. Lerner, and E. Gaetjens, Antiproliferative effects of 4', 5'–unsaturated adenine nucleosides on leukemia L 1210 cells in vitro, *Experientia* 45 (1989), Birkhäuser Verlag, CH–4010 Basel/Switzerland, pp. 729–730.

Leon B. Lerner, Synthesis of 9–α– and 9–βandD–fucopyranosyladenine, *Carbohydrate Research*, 19 (1971) pp. 255–258.

Leon M. Lerner, Bertrum Sheid, and Eric Gaetjens, Preparation and Antileukemic Screening of Some New 6'–Deoxyhexopyranosyladenine Nucleosides, *Journal of Medicinal Chemistry* (1987), vol. 30, No. 8, pp. 1521–1525.

Linda V. Fisher, William W. Lee and Leon Goodman, Some 6–Substituted–9–(β–L–fucopyranosyl) purines (1), (1969), Journal of Heterocyclic Chemistry, vol. 6, p. 949.

Leon M. Lerner, Interconversions of Hexofuranosyl Nucleosides. IV. Synthesis of Nucleosides Derived from 6–Deoxy–L–glucose, *J. Org. Chem.*, vol. 37, No. 26 (1972), pp. 4386–4391.

Leon M. Lerner, Interconversions of Hexofuranosyl Nucleosides. V. Synthesis and Reexamination of the Structure of 9–(6–Deoxy–α–L–mannofuranosyl) adenine, *J. Org. Chem.*, vol. 38, No. 21 (1973), pp. 3704–3709.

Leon M. Lerner, Interconversions of Hexofuranosyl Nucleosides. I. Synthesis of 9–β–L–Gulofuranosyladenine from 9–α–D–Mannofuranosyladenine, *J. Org. Chem.*, vol. 37, No. 3 (1972), pp. 470–481.

Leon M. Lerner, Synthesis of 9–α–D–rhamnofuranosyladenine, *Carbohydrate Research*, 38 (1974) 328–332.

B. Sheid, E. Gaetjens, S. T. Chung, and L. M. Lerner, Enzymatic formation of potential anticancer and antiviral inoside analogues, *Experientia* 52 (1996), Birkhäuser Verlag, CH–4010 Basel/Switzerland, pp. 878–881.

Bertrum Sheid, Mitu Saggar, Eric Gaetjens, and Leon M. Lerner, Antiproliferative activity of purine nucleoside dialdehydes against leukemia L1210 in vitro, *Caner Chemotherapy and Pharmacology* (1991) 28, pp. 339–343.

Linda V. Fisher, William W. Lee and Leon Goodman, Some 6–Substituted–9–(β–L–fucopyranosyl) purines (1), *Journal of Hetocyclic Chemistry*, vol. 6, (1969), p. 949.

*Primary Examiner*—David Guzo
*Assistant Examiner*—Mark L. Shibuya
*Attorney, Agent, or Firm*—Allen, Dyer, Doppelt, Milbath & Gilchrist, P.A.

[57] ABSTRACT

An antiretroviral composition for inhibiting the action of reverse transcriptase include a nucleoside analog containing a six-carbon levo hexose sugar, for example, L-rhamnose or L-fucose. Treatment is achieved by delivering the antiretroviral to the infected system, wherein the reverse transcription process is inhibited via steric hindrance, halting the viral RNA replication. Delivery may be accomplished by conventional methods, such as via oral dosing or injection. Additional delivery methods are also contemplated, including packaging in liposomes and protein targeting. The composition and method are also useful for inhibiting the proliferation of cancer cells by halting the transcription process.

6 Claims, 10 Drawing Sheets

HIV RNA SECTION 822-847

COMPLETED RNA/DNA OF HIV SECTION

1' ADENYL-L-RHAMNOSE

1' CYTODINYL-L-RHAMNOSE

1'-GUANYL-L-RHAMNOSE

1'-THYMIDYL-L-RHAMNOSE

1'-URIDINYL-L-RHAMNOSE

ADENOSINE ANALOG SHOWING RT INHIBITION

ADENOSINE ANALOG SHOWING STERIC HINDRANCE

CYTIDINE ANALOG SHOWING RT INHIBITION

CYTIDINE CAUSING STERIC HINDRANCE

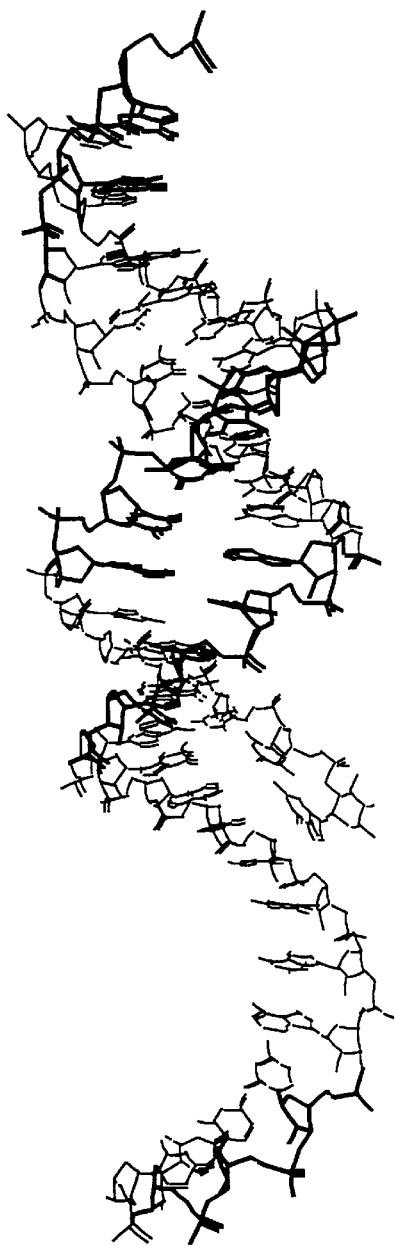
FIG. 12 GUANOSINE ANALOG SHOWING RT INHIBITION
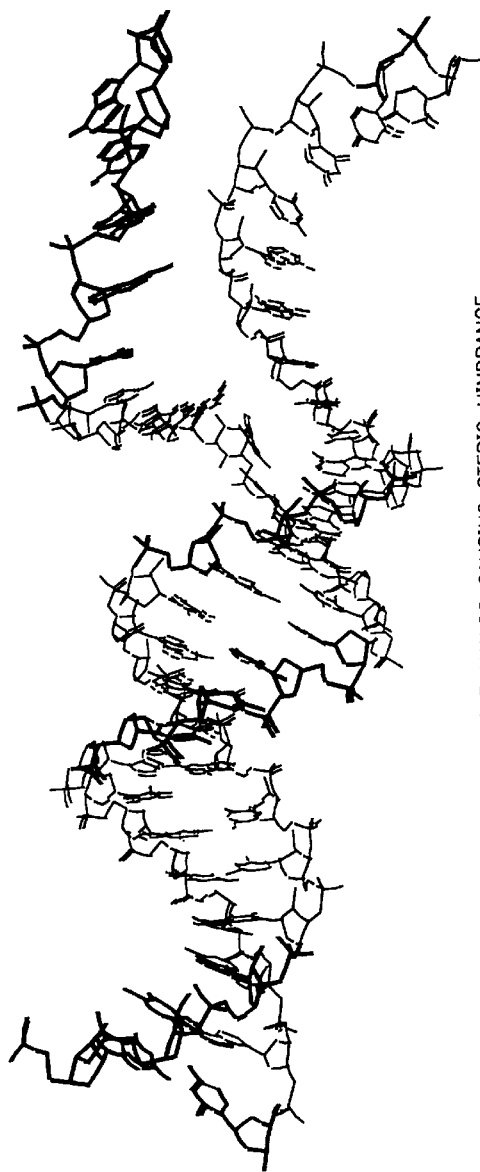
FIG. 13 GUANOSINE ANALOG CAUSING STERIC HINDRANCE

THYMIDINE ANALOG SHOWING RT INHIBITION

THYMIDINE ANALOG SHOWING STERIC HINDRANCE

URACIL SHOWING RT INHIBITION

URIDINE ANALOG SHOWING STERIC HINDRANCE

LEVO-MONOSACCHARIDE IN A NUCLEOSIDE ANALOG FOR USE AS AN ANTI-RETROVIRAL AGENT

BACKGROUND OF THE INVENTION

1. Field of the Invention

The present invention relates to compositions and methods for inhibiting reverse transcription, and, more particularly, to such compositions and methods for creating a nucleoside analog that disrupts the hybridization step during reverse transcription.

2. Description of Related Art

Retroviruses contain RNA rather than DNA as the genetic material. Those such as that believed responsible for acquired immune deficiency syndrome (AIDS), the human immunodeficiency virus (HIV), function by utilizing the enzyme RNA-dependent DNA polymerase, or reverse transcriptase, to create a DNA strand from the viral RNA for directing viral infection and synthesis within a host system.

It is well known in the art to introduce nucleoside analogs into the host that block reverse transcription from manufacturing DNA by presenting faulty substrates to the enzyme that compete with the naturally occurring nucleosides for incorporation into a DNA strand. For example, azidothymidine (AZT; Retrovir, Burroughs Wellcome) is widely used in cases of HIV infection.

A suggestion has also been made to use L-nucleosides as analogs. Weis et al. (U.S. Pat. Nos. 5,559,101 and 5,672,594) disclose the use of L-ribofuranosyl nucleosides as an antiviral composition.

Lin et al. (U.S. Pat. Nos. 5,561,120; 5,627,160; and 5,631,239) teach the use of dideoxynucleoside analogs containing a dideoxy ribofuranosyl moiety having an L-configuration as an anti-retroviral agent, particularly for HBV. The '160 patent additionally discloses the use of 1-(2,3)-dideoxy-β-L-ribofuranosyl)-5-fluorocytosine as a potent anti-HIV agent.

Chu et al. (U.S. Pat. Nos. 5,565,438; 5,567,688; and 5,587,362) describe L-nucleoside analogs for treatment of HBV or EBV. The sugar moiety illustrated comprises a 5-membered 2'-fluorinated ring.

It is known, however, that at least some of the previously tested antiviral agents have negative side effects such as cytotoxicity and also limited effectiveness owing to inactivation or digestion prior to reaching the target.

SUMMARY OF THE INVENTION

It is therefore an object of the present invention to provide an effective antiretroviral agent.

It is an additional object to provide such an agent that has reduced cytotoxicity over previously known compositions.

It is a further object to provide such an agent whose mode of action facilitates effective dosing.

It is another object to provide a method of inhibiting reverse transcriptase.

It is yet an additional object to provide a method of introducing an antiretroviral agent into a host cell.

It is yet a further object to provide a method of targeting a host cell for delivery of an antiretroviral agent.

It is yet another object to provide a method for making an antiretroviral agent.

It is an additional object to provide a method of making a delivery system for an antiretroviral agent.

It is a further object to provide a composition effective in treating cancers.

It is another object to provide a method of treating cancers.

These objects and others are attained by the present invention, compositions and associated methods for inhibiting the action of reverse transcriptase in a system containing retroviral material, such as a cell infected with a retrovirus. The antiretroviral agent in a particular embodiment of the invention comprises a nucleoside/nucleotide analog containing a six-carbon levo hexose sugar, for example, L-rhamnose. Shown below are the structures of L-rhamnose and L-fucose in two dimensions and in the chair configuration (hydrogens are omitted for clarity except in the case of the two-dimensional rhamnose structure).

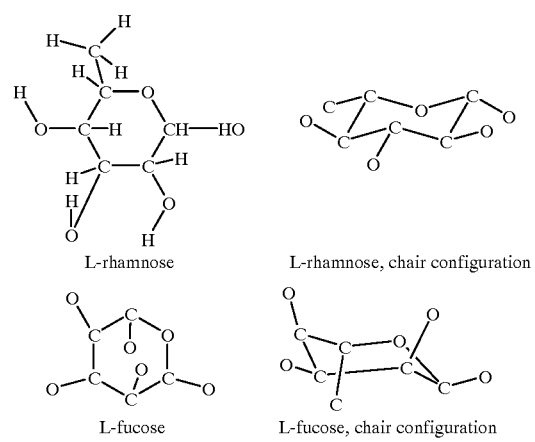

L-rhamnose      L-rhamnose, chair configuration

L-fucose      L-fucose, chair configuration

This particular sugar is not intended to be limiting, however, and other six-carbon levo hexose sugars are also intended to be subsumed herein, such as other hexoses that are able to be synthesized in a levo conformation.

The treatment method comprises delivering the antiretroviral agent to the infected system, wherein the reverse transcription process is inhibited, halting the viral RNA replication and, hence, the infection. The means by which the inhibition occurs is believed to be by steric hindrance, wherein the reverse transcription process is prevented from elongating a complementary DNA strand from a point at which the nucleoside analog is incorporated, although this is not intended as a limitation.

Delivery may be accomplished by conventional methods, such as via oral dosing or injection.

Additional delivery methods are also contemplated, including packaging in liposomes and protein targeting.

Similarly, the spread of cancer can be inhibited by introducing a levo hexose into the cancer cell, the incorporation of which into a nucleic acid strand during transcription inhibits the continuation thereof, thus inhibiting cell division.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 12 illustrates the halting of reverse transcription at the site of the introduction of a guanosine analog of FIG. 5.

FIG. 13 illustrates an attempt at continuation of hybridization following the introduction of a guanosine analog as in FIG. 12.

DETAILED DESCRIPTION OF THE PREFERRED EMBODIMENTS

Figure 1:
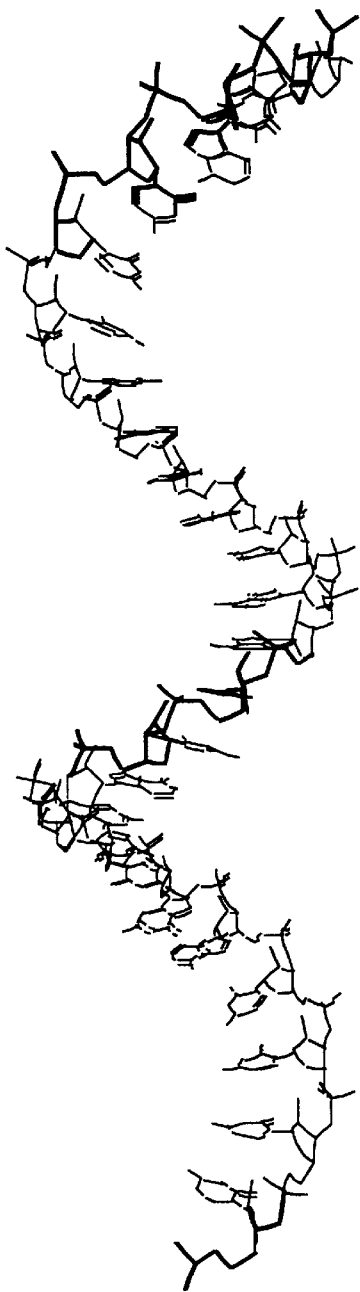
FIG. 1 (prior art) illustrates a segment of HTLV-III (HIV) RNA bases 822–847.
Figure 2:
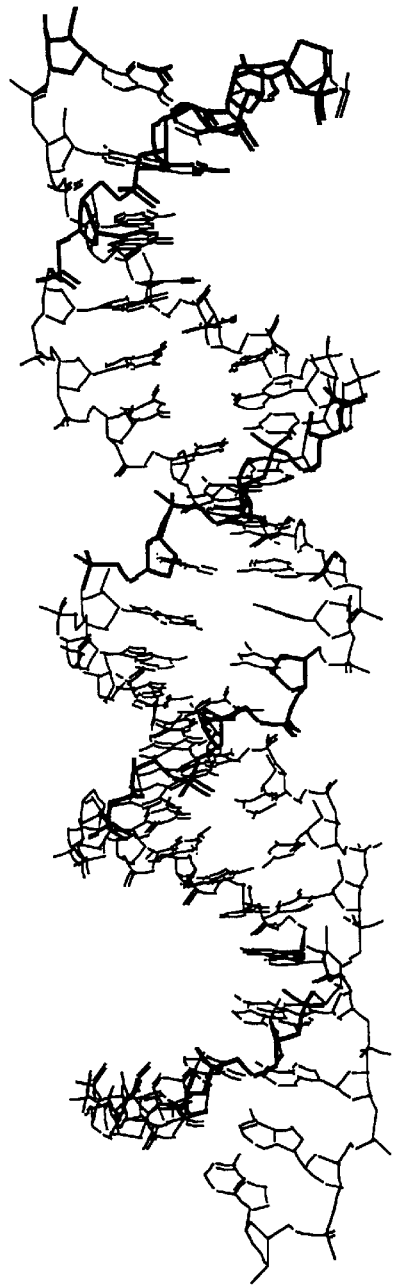
FIG. 2 (prior art) illustrates a segment of HTLV-III (HIV) RNA-DNA hybrid bases 822–847.
Figure 3:
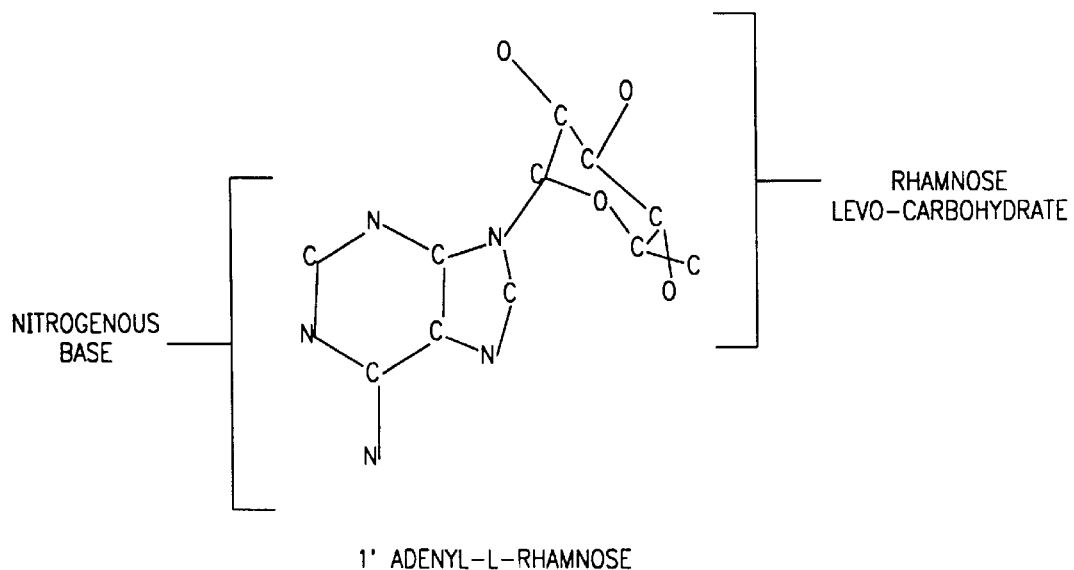
FIG. 3 illustrates the structure of 1'-adenyl-L-rhamnose.
Figure 4:
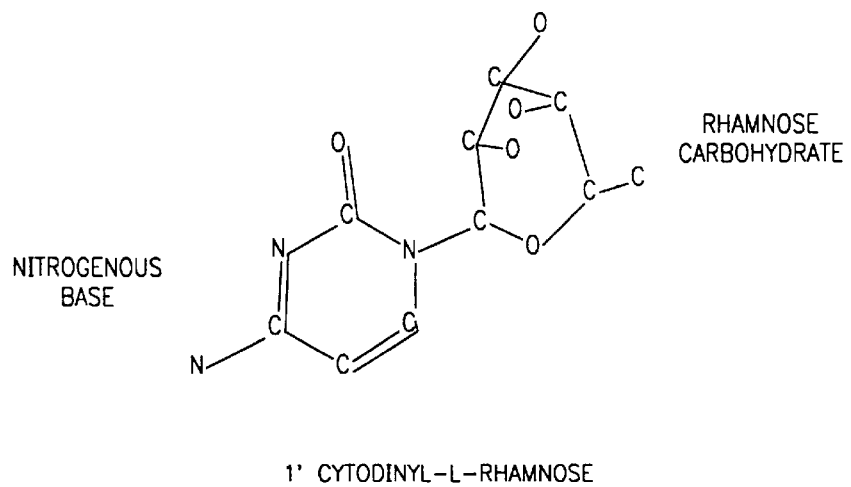
FIG. 4 illustrates the structure of 1'-cytodinyl-L-rhamnose.
Figure 5:
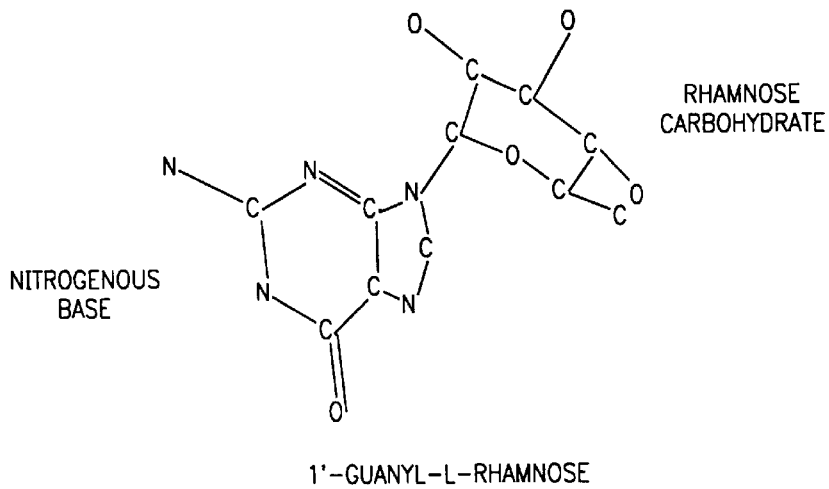
FIG. 5 illustrates the structure of 1'-guanyl-L-rhamnose.
Figure 6:
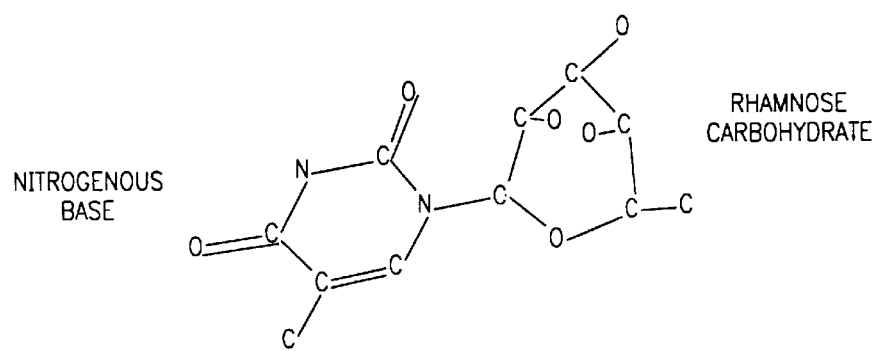
FIG. 6 illustrates the structure of 1'-thymidyl-L-rhamnose.

A description of the preferred embodiments of the present invention will now be presented with reference to FIGS. 1–18. HIV will be used as an exemplary system herein for illustrative purposes, but this is not intended as a limitation. FIG. 1 illustrates a segment of HTLV-III (HIV) RNA bases 822–847, as reported by Ratner et al. (*Nature* 313, 277, 1985); FIG. 2 illustrates the same RNA segment hybridized with a complementary segment of DNA, such as would be expected following reverse transcription. In the following this segment will be used for computer modeling of the inhibition of reverse transcription by the compositions of the present invention.

Figure 7:
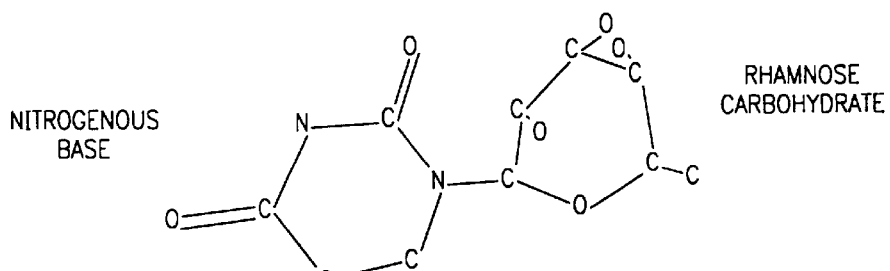
FIG. 7 illustrates the structure of 1'-uridinyl-L-rhamnose.
Figure 8:
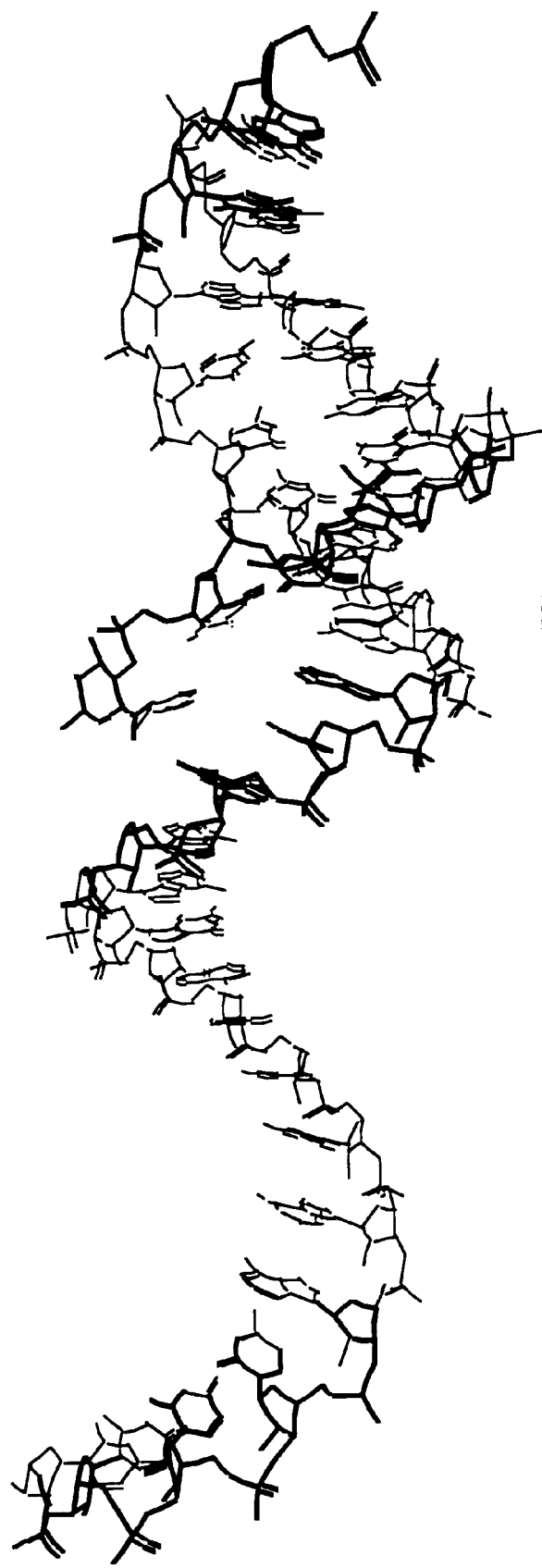
FIG. 8 illustrates the halting of reverse transcription at the site of the introduction of an adenosine analog of FIG. 3.
Figure 9:
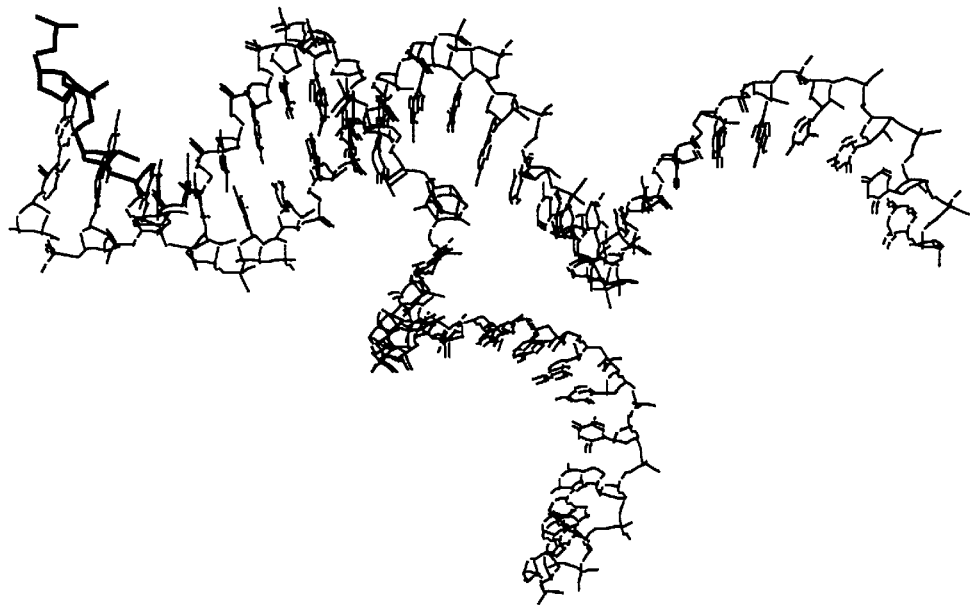
FIG. 9 illustrates an attempt at continuation of hybridization following the introduction of an adenosine analog as in FIG. 8.
Figure 10:
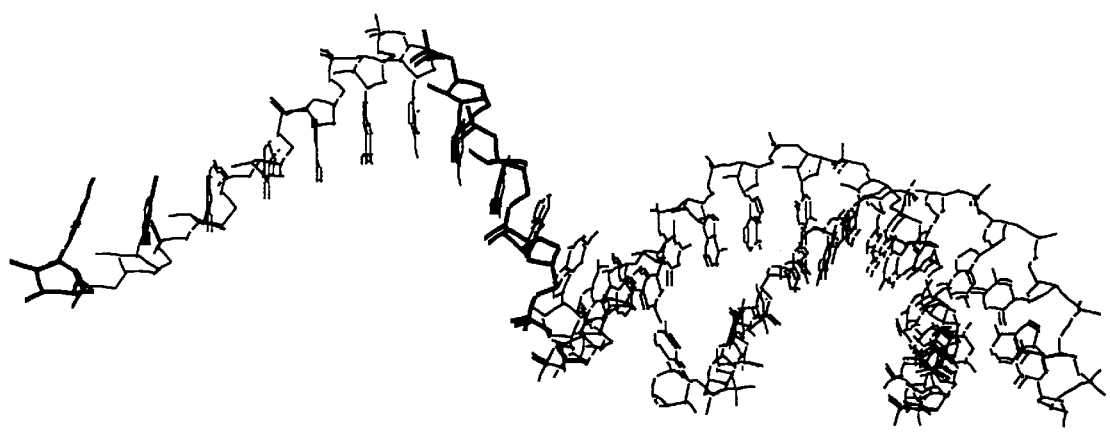
FIG. 10 illustrates the halting of reverse transcription at the site of the introduction of a cytidine analog of FIG. 4.
Figure 11:
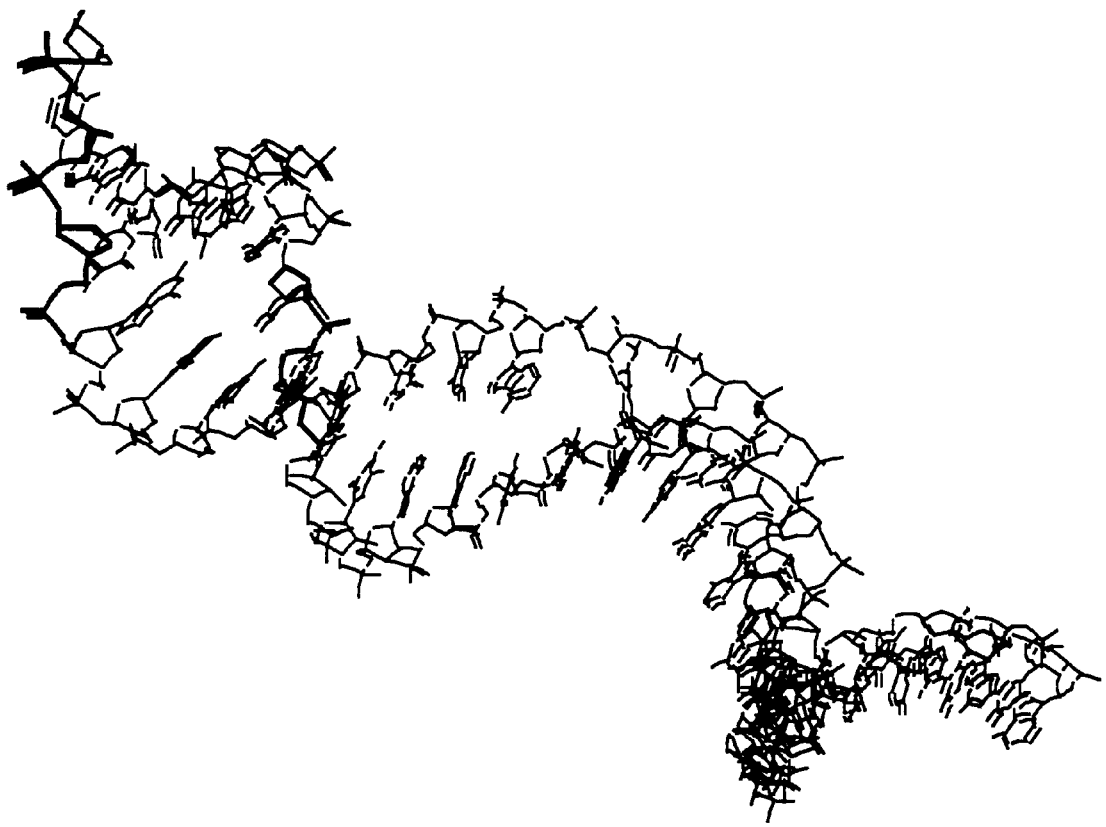
FIG. 11 illustrates an attempt at continuation of hybridization following the introduction of a cytidine analog as in FIG. 10.
Figure 14:
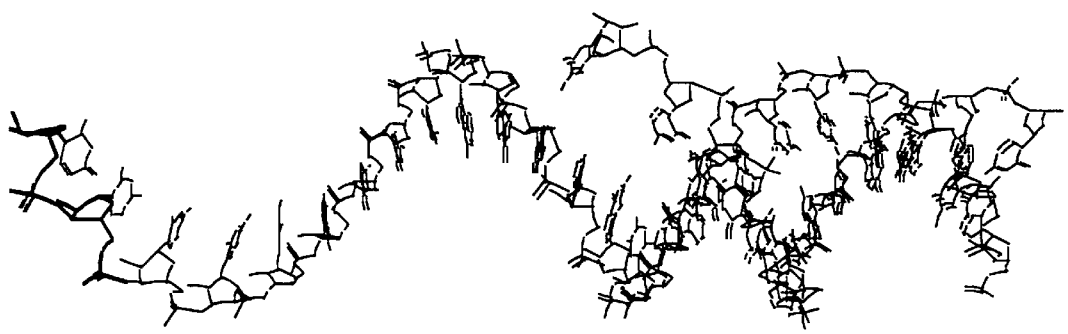
FIG. 14 illustrates the halting of reverse transcription at the site of the introduction of a thymidine analog of FIG. 6.
Figure 15:
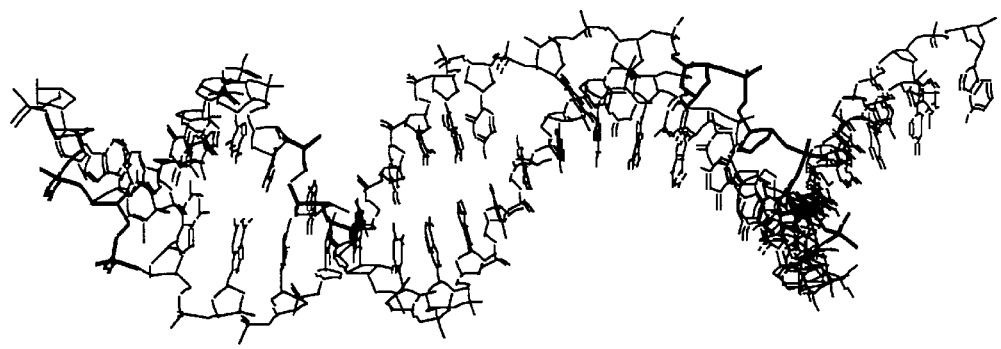
FIG. 15 illustrates an attempt at continuation of hybridization following the introduction of a thymidine analog as in FIG. 14.
Figure 16:
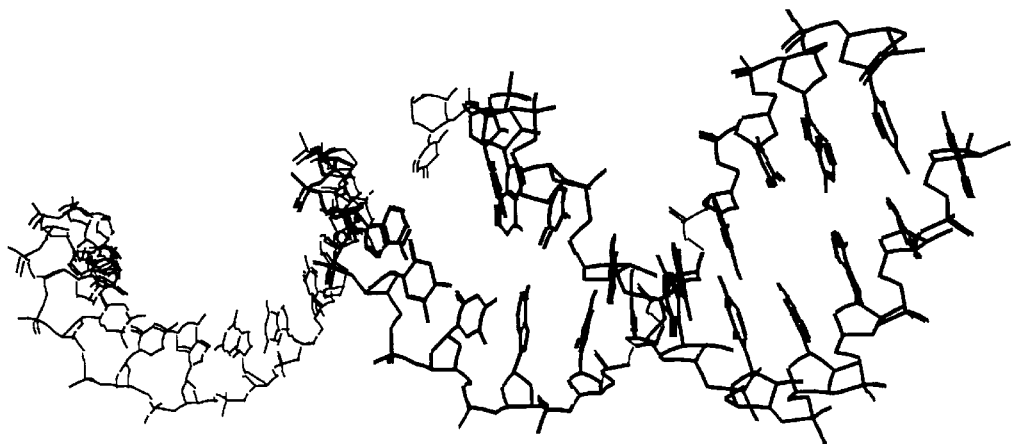
FIG. 16 illustrates the halting of reverse transcription at the site of the introduction of a uridine analog of FIG. 7.
Figure 17:
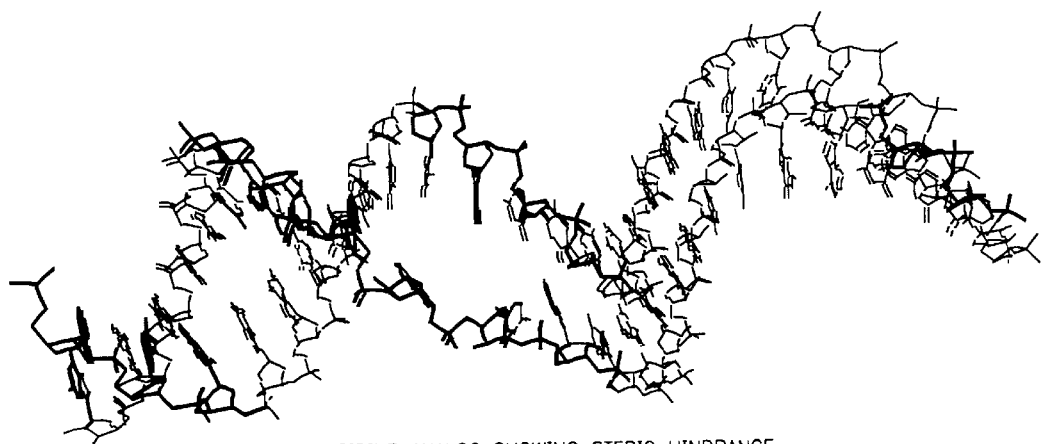
FIG. 17 illustrates an attempt at continuation of hybridization following the introduction of a uridine analog as in FIG. 16.
Figure 18:
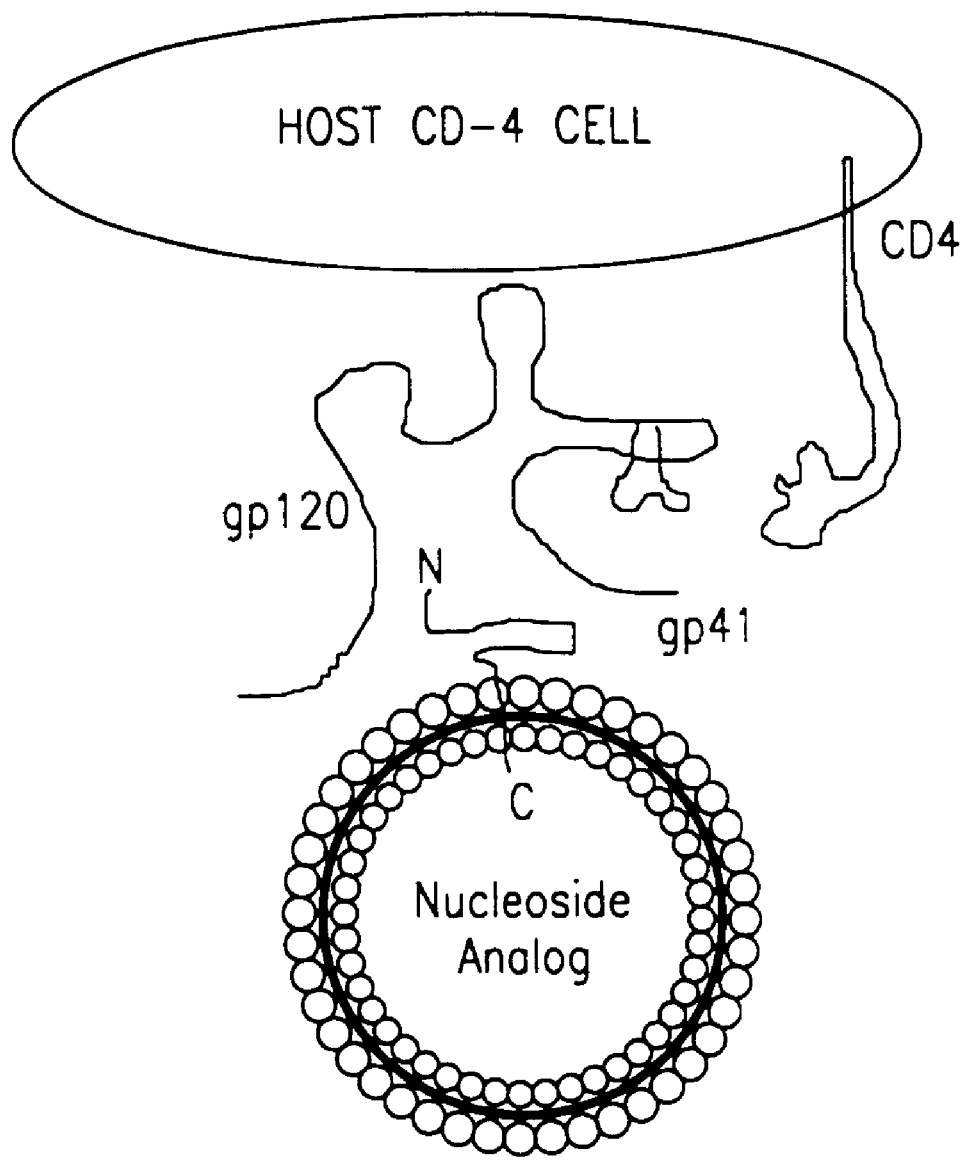
FIG. 18 illustrates the delivery of the nucleoside analog to a host cell with a liposome.

In a preferred embodiment, an agent for inhibiting the reverse transcription process in a system infected with a retrovirus comprises a nucleoside analog containing a six-carbon levo hexose sugar, such as the L-monosaccharide L-rhamnose. The nucleoside analog is synthesized from at least one of a group of bases consisting of adenine, cytodine, guanine, thymidine, and uridine to form, respectively, 1'-adenyl-L-rhamnose (FIG. 3), 1'-cytodinyl-L-rhamnose (FIG. 4), 1'-guanyl-L-rhamnose (FIG. 5), 1'-thymidyl-L-rhamnose (FIG. 6), and 1'-uridinyl-L-rhamnose (FIG. 7). It should also be noted that the nucleoside analogs may be synthesized at a position other than 1', which are intended as exemplary embodiments. The nitrogenous bases can assume any of the $\alpha$, $\beta$, syn, and anti orientations to the levo-monosaccharide moiety.

Once within the cell, the nucleoside analog is phosphorylated in the cell via the action of a kinase to form a phosphate nucleotide analog. The analog is typically in the triphosphate form, but the mono- and diphosphate forms are also acceptable. This phosphorylation may occur at the 4' position, but this is not intended as a limitation. The nucleotide analog competes with naturally occurring nucleotides for incorporation into a DNA strand that is complementary to the retroviral RNA by the action of reverse transcriptase via known biochemical pathways.

As soon as one of the bases containing the nucleotide analog is incorporated, further reverse transcription is inhibited. This inhibition is believed to occur by steric hindrance, as indicated by molecular modeling studies performed for each of the above-listed rhamnose moieties. In each of the succeeding pairs of FIGS. 8–17 is illustrated the inhibition of RNA/DNA hybridization at the point of incorporation of one of the nucleotide analogs of the present invention and an attempt to force a continuation of hybridization beyond the incorporation site. It can be seen in FIGS. 9, 11, 13, 15, and 17 that a divergence of the strands at the incorporation site prevents their achieving the necessary proximity to form a double-stranded hybrid. In the case of the cytidine analog (FIG. 11), the bases appear to orient in a coplanar manner. For the uridine analog (FIG. 17), the bases are positioned "behind" the backbone in the model.

One of the drawbacks of AZT therapy has been its high degree of metabolism prior to acting as an RT inhibitor. The compounds of the present invention are not believed to suffer this drawback, as naturally occurring degradation enzymes are not effective in catabolizing levo sugars. Thus the compounds of the present invention have greater stability, providing enhanced efficacy, and also permitting more accurate dosing.

The compounds of the present invention may be delivered by conventional methods, such as orally or by injection. The compounds may also be delivered in phosphorylated form, preferably with buffering agents, orally or by injection. One additional delivery method is contemplated for the compounds: liposomal suspension.

Methods for achieving liposomal encapsulation of a pharmaceutical composition are known in the art. An exemplary method anticipated for the present invention (FIG. 18), which is for delivering an antiretroviral agent to an infected host cell, comprises the steps of combining an antiretroviral agent with a delivery means, wherein the antiretroviral agent comprises an adenosine analog having a six-carbon levo sugar moiety. In this exemplary embodiment the delivery means comprises a liposome, and the combining step comprises packaging the antiretroviral agent into the liposome. Next the delivery means is introduced into a system containing a cell infected with a retrovirus. Finally, the delivery means is permitted to contact the cell and to deliver the antiretroviral agent into the cell interior.

In a particular embodiment, wherein the host cell is infected with HIV, the introducing step comprises the steps of attaching a gp120/gp41 adhesin complex of an HIV virus to the liposome, such that at least a CD4 binding site of the gp120 lies outside the liposome. Next the CD4 binding site is permitted to bind to a CD4 external to the HIV-infected host cell, which causes a conformational change in the gp120, which in turn causes the liposome and host cell membranes to fuse. This fusion permits a comingling of the host cell and liposome contents, thus effecting a delivery of the antiretroviral agent into the host cell.

It may be appreciated by one skilled in the art that additional embodiments may be contemplated, including similar compositions and methods for treating cancer by inhibiting replication of cancer cells during transcription and metastasis. Delivery methods of such compositions include those as discussed above.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the compositions and methods illustrated and described herein are by way of example, and the scope of the invention is not limited to the exact details of structure, synthesis, and delivery.

Having now described the invention, the construction, the operation and use of preferred embodiments thereof, and the advantageous new and useful results obtained thereby, the new and useful compositions and methods, and reasonable biochemical equivalents thereof obvious to those skilled in the art, are set forth in the appended claims.

What is claimed is:

1. A method of inhibiting hybridization of a reverse-transcribing DNA strand with an RNA template comprising the steps of:

delivering at least one nucleoside analog containing an L-rhamnose moiety to the RNA template, wherein the nucleoside analog is selected from the group consisting of 1'-adenyl-L-rhamnose, 1'-cytodinyl-L-rhamnose, 1'-guanyl-L-rhamnose, 1'-thymidyl-L-rhamnose, and 1'-uridinyl-L-rhamnose;

wherein the nucleoside analog is phosphorylated into a nucleotide to form a nucleotide analog;

wherein the nucleotide analog is incorporated into DNA synthesized during reverse transcription of the RNA template; and wherein hybridization between the reverse-transcribed DNA and the RNA template is inhibited by the presence of the incorporated nucleotide analog.

2. The method recited in claim 1, wherein in the hybridization inhibition step the L-rhamnose moiety contained in the incorporated nucleotide analog sterically hinders the reverse-transcribed DNA from hybridizing with template RNA.

3. A method of inhibiting hybridization of a reverse-transcribed DNA strand with an RNA template comprising the steps of:

providing a DNA strand having a nucleotide analog incorporated therein, wherein:

the nucleotide analog comprises a phosphorylated nucleoside, the nucleoside including an L-rhamnose moiety, the L-rhamnose moiety selected from a group consisting of 1'-adenyl-L-rhamnose, 1'-cytodinyl-L-rhamnose, 1'-guanyl-L-rhamnose, 1'-thymidyl-L-rhamnose, and 1'-uridinyl-L-rhamnose; and the DNA comprises DNA synthesized during reverse transcription of an RNA template;

wherein further hybridization between the DNA and the RNA template is inhibited by the presence of the incorporated nucleotide analog.

4. The method recited in claim 3, wherein in the hybridization inhibition step the L-rhamnose moiety contained in the incorporated nucleotide analog sterically hinders the reverse-transcribed DNA from hybridizing with the template RNA.

5. A method of inhibiting hybridization of a reverse-transcribing DNA strand with an RNA template comprising the steps of:

delivering at least one nucleoside analog containing an L-rhamnose moiety to the RNA template, wherein the nucleoside analog is selected from the group consisting of 1'-adenyl-L-rhamnose, 1'-cytodinyl-L-rhamnose, 1'-guanyl-L-rhamnose, 1'-thymidyl-L-rhamnose, and 1'-uridinyl-L-rhamnose;

wherein the nucleoside analog is incorporated into DNA synthesized during reverse transcription of the RNA template; and wherein hybridization between the reverse-transcribed DNA and the RNA template is inhibited by the presence of the incorporated nucleoside analog.

6. The method recited in claim 5, wherein in the hybridization inhibition step the L-rhamnose moiety contained in the incorporated nucleoside analog sterically hinders the reverse-transcribed DNA from hybridizing with template RNA.

* * * * *